United States Patent
Davies (10) Patent No.: US 11,786,335 B2
(45) Date of Patent: Oct. 17, 2023

(54) APPARATUS AND METHOD FOR ASSISTING TOOL USE

(71) Applicant: SIGNATURE ROBOT LIMITED, London (GB)

(72) Inventor: Brian Lawrence Davies, London (GB)

(73) Assignee: Kilburn & Strode LLP, London (GB)

( * ) Notice: Subject to any disclaimer, the term of this patent is extended or adjusted under 35 U.S.C. 154(b) by 346 days.

(21) Appl. No.: 16/332,596

(22) PCT Filed: Sep. 12, 2017

(86) PCT No.: PCT/GB2017/052679
§ 371 (c)(1),
(2) Date: Mar. 12, 2019

(87) PCT Pub. No.: WO2018/046969
PCT Pub. Date: Mar. 15, 2018

(65) Prior Publication Data
US 2019/0290390 A1    Sep. 26, 2019

(30) Foreign Application Priority Data
Sep. 12, 2016   (GB) ..................................... 1615438

(51) Int. Cl.
*A61B 90/60*    (2016.01)
*A61B 34/30*    (2016.01)
(Continued)

(52) U.S. Cl.
CPC .............. *A61B 90/60* (2016.02); *A61B 34/30* (2016.02); *A61B 90/03* (2016.02); *B25J 1/02* (2013.01);
(Continued)

(58) Field of Classification Search
CPC ......... A61B 18/10; A61B 18/12; A61B 18/14; A61B 34/76
See application file for complete search history.

(56) References Cited

U.S. PATENT DOCUMENTS

2006/0142657 A1    6/2006  Quaid et al.
2011/0118748 A1*   5/2011  Itkowitz ................. A61B 34/30
                                                              606/130
(Continued)

FOREIGN PATENT DOCUMENTS

| EP | 1 629 949 A2 | 3/2006 |
|----|--------------|--------|
| JP | 59-146770 A  | 8/1984 |

(Continued)

OTHER PUBLICATIONS

PCT International Search Report and Written Opinion of the ISA for PCT/GB2017/052679 dated Dec. 1, 2017, 19 pages.
(Continued)

*Primary Examiner* — Michael J D'Abreu
(74) *Attorney, Agent, or Firm* — Patterson Thuente PA (57) ABSTRACT

Apparatus and related methods for assisting tool use includes one or more motors, a wrist support and a shaft coupled to the one or more motors. The shaft includes a coupling to couple to a tool to enable a user resting a hand with the wrist on the wrist support to hold and manipulate the tool with one or more fingers. The apparatus can include a controller configured to: receive position data indicative of a position of an active end of the tool; receive constraint data indicative of one or more regions of space in which the active end should not be positioned; and process the position and constraint data to control the one or more motors to bias the active end out of a region indicated by the constraint data when a position indicated by the position data is within the region indicated by the constraint data.

15 Claims, 4 Drawing Sheets

(51) Int. Cl.
*A61B 90/00* (2016.01)
*B25J 1/02* (2006.01)
*B25J 9/16* (2006.01)
A61B 34/20 (2016.01)
A61B 17/00 (2006.01)
A61B 34/00 (2016.01)

(52) U.S. Cl.
CPC .............. *B25J 9/1676* (2013.01); *A61B 34/76* (2016.02); *A61B 2017/00725* (2013.01); *A61B 2034/2059* (2016.02); *A61B 2560/0223* (2013.01)

(56) References Cited

U.S. PATENT DOCUMENTS

| 2012/0083652 | A1 | 4/2012 | Langlois | |
|---|---|---|---|---|
| 2014/0222023 | A1* | 8/2014 | Kim | A61B 34/76 606/130 |
| 2017/0202605 | A1* | 7/2017 | Shelton, IV | A61B 18/1445 |
| 2017/0209737 | A1* | 7/2017 | Tadi | A61H 1/0288 |

FOREIGN PATENT DOCUMENTS

| JP | 07-195281 A | 8/1995 |
|---|---|---|
| JP | 2014-109818 A | 6/2014 |
| JP | 2015-128681 A | 7/2015 |
| WO | WO 98/16164 A1 | 4/1998 |
| WO | WO 2002/060653 A2 | 8/2002 |
| WO | WO 2002/061688 A2 | 8/2002 |
| WO | WO 2002/061709 A1 | 8/2002 |
| WO | WO 2003/043 515 A1 | 5/2003 |
| WO | WO 2003/043504 A2 | 5/2003 |
| WO | WO 2004/021909 A1 | 3/2004 |
| WO | WO 2006/048651 A1 | 5/2006 |
| WO | WO 2007/045810 A2 | 4/2007 |
| WO | WO 2011/021192 A1 | 2/2011 |
| WO | WO 2012/080694 A1 | 6/2012 |

OTHER PUBLICATIONS

GB Combined Search and Examination Report for GB 1615438.7, dated Feb. 23, 2017, 5 pages.

John Albert Beckman et al: "The Phantom Omni as an underactuated robot". Jan. 1, 2007 (Jan. 1, 2007). XP055427753. ISBN: 978-0-549-33365-4 Retrieved from the Internet: URL:http://lib.dr.iastate.edu/cgi/viewcontent.cgi?article=16109&context=rtd [retrieved on Nov. 22, 2017] Iowa State University, 94 pages.

S. A. Bowyer, B. L. Davies, F. Rodriguez y Baena, "Active Constraints/Virtual Fixtures: A Survey", IEEE Transactions on Robotics, vol. 30, No. 1, pp. 138-157, Feb. 2014.

S. C. Ho, R.D. Hibberd and B.L. Davies, "Robot Assisted Knee Surgery, Establishing a force control strategy incorporating action motion constraint", IEEE Engineering in Medicine and Biology, May/Jun. 1995, p. 292-300.

English translation of Notification of Reasons for Refusal for JP 2019-535987, dated Jun. 1, 2011, 7 pages.

Notification of Reasons for Refusal for JP 2019-535987, dated Jun. 1, 2011, 4 pages.

* cited by examiner

APPARATUS AND METHOD FOR ASSISTING TOOL USE

RELATED APPLICATIONS

This application is a National Phase entry of PCT Application No. PCT/GB2017/052679, filed Sep. 12, 2017, which claims priority from Great Britain Application No. 1615438.7 filed Sep. 12, 2016 the disclosures of which are hereby incorporated by referenced herein in their entirety.

FIELD OF THE INVENTION

The present disclosure relates to an apparatus and method to assist with the use of a tool, for example a cutting or burr tool. Specifically, although not exclusively, the present disclosure relates to a surgical robot for assisting with the use of a surgical tool.

BACKGROUND

Robot-assisted tool use is known to be employed in several areas where direct use of a tool by a human is disadvantageous. One example occurs in radioactive environments where a remotely controlled robot can reproduce tool use movements made by a user in a remote location. Another example is robotic surgery, where a robot replicates movements made by a surgeon interacting with a user interface, for example to enable easier access in minimally invasive surgery or to allow fine control of movements by scaling down movement magnitudes. Surgical robots can also be employed to help with operative planning by registering a robot coordinate system to a patient coordinate system. The robot can then guide the surgeon, for example by applying active constraints (a "virtual wall") that limit the region where a tool attached to the robot can be used so that damage to surrounding tissues can be avoided. See S. A. Bowyer, B. L. Davies, F. Rodriguez y Baena, IEEE Transactions on Robotics, Vol. 30, No. 1, page 138, February 2014; WO2002/060653; WO2003/043515; S. C. Ho, R. D. Hibberd and B. L. Davies, IEEE Engineering in Medicine and Biology, May/June 1995, page 292; all incorporated herein by reference.

SUMMARY

Some aspects of the disclosure are set out in the independent claims. Optional features of disclosed embodiments are set out in the dependent claims.

In some aspects, there is provided an apparatus for assisting tool use. The apparatus comprises one or more motors, a wrist support and a shaft coupled to the one or more motors, for example in a direct drive, or geared configuration, or in a cable or belt drive configuration. The shaft comprises a coupling to couple to a tool, for example a cutting, drilling, burring, heating or other material shaping tool, or a measuring tool, to enable a user resting a hand with the wrist on the wrist support to hold and manipulate the tool with two or more fingers of the hand. The apparatus further comprises a controller configured to:

receive position data indicative of a position of an active end of a tool coupled to the coupling;

receive constraint data indicative of one or more regions of space in which the active end of the tool should not be positioned; and process the position and constraint data to control the one or more motors to bias the active end of the tool out of a region indicated by the constraint data when a position indicated by the position data is within the region indicated by the constraint data.

Advantageously, the apparatus exploits the high accuracy of finger movements to enable robotically assisted precision tool use at a small scale while providing constraints to keep the active end within a working region while the tool is used. Fine and precise finger movements are further facilitated by resting the wrist in a fixed position. It will be understood that the active end of a tool is the end where the tool interacts with a material, e.g. to shape the material. For example, the active end of a cutting tool may be a blade or burr.

In some embodiments, the one or more motors are back driveable, thereby enabling a user to move a tool attached to the coupling without energising the one or more motors. Preferably the resistance is substantially the same across the motors/actuators, so as not to bias user movements. Advantageously, this simplifies the control of the one or more motors, since the motors only need to provide the forces/torques needed to generate the active constraints, that is to generate the forces/torques to bias the active end out of the region indicated by the constraint data, while the user directly controls the movement of, and force applied by, the tool. In other embodiments, in which the motors are not back-driveable, a net force/torque generated by a user on the tool and hence the coupling may be sensed and the motors controlled to generate forces/torques to replicate or assist the user applied force.

In line with the manipulation by a user's fingers with the wrist supported, a largest distance between two positions of the active end within the range of movement may be less than 10 cm, optionally less than 5 cm, 4 cm or 3 cm. Additionally, or instead, the apparatus may in some embodiments be configured to mechanically constrain a range of movement of the coupling so that a largest distance between two positions of the coupling within the range of movement is less than 10 cm, optionally less than 5 cm, 4 cm or 3 cm. It will be understood that any combination of mechanical and active constraints is possible and is hereby disclosed. In particular, a range of 4 or 5 cm is pertinent as this corresponds to a typical range of motion of fingers in a precision grip with the wrist fixed.

In some embodiments, the shaft has at least one linear and at least one rotational degree of freedom. For example, the shaft may have three degrees of freedom comprising at least one linear and at least one rotational degree of freedom, for example one linear and two rotational degrees of freedom. The at least one linear degree of freedom may comprise a degree of freedom along a direction towards and away from the wrist support.

In some embodiments, the one or more motors are disposed in a housing and the wrist support is part of or is secured in relation to, for example secured to, the housing. For example, in some embodiments the wrist support is on top of the housing when the apparatus is used and the one or more motors are disposed in the housing below the wrist support, with the shaft protruding through an opening in a top wall of the housing. The wrist support may be provided in the form of a cushion or pad in a defined relationship with the one or more motors, for example secured to an aspect of the housing if present, or may simply be a surface of the housing. The wrist support may in some embodiments comprise a strap or other arrangement for securing the user's hand relative to the support.

In some embodiments, the apparatus comprises one or more position encoders, for example absolute or relative encoders, each of the one or more motors being associated with a position encoder from which a configuration of the shaft along a corresponding degree of freedom can be determined. In these embodiments, receiving position data comprises:

receiving encoder data from the one or more position encoders;

receiving calibration data indicative of a relationship between data from the one or more position encoders and the active end of the tool; and using the encoder and calibration data to obtain the position data.

In embodiments where relative encoders are used, a zeroing step at the start of operation may be required.

In other embodiments, position data is captured using an optical position sensing system, for example including a number of markers secured to the tool or shaft and a camera system.

In some embodiments, the tool may be a surgical tool. The constraint and position data may be in a coordinate system registered to an object to be worked on with the tool, for example a part of a patient in the case of surgical tools. In some embodiments, the apparatus may be configured as a surgical robot.

In some embodiments, the controller may be configured to process the position and constraint data to cause generation of a control signal for the tool to deactivate the active end when a position indicated by the position data is within a region indicated by the constraint data. It will be understood that deactivating the active end may comprise sending a signal to the tool to switch the tool off (e.g. stop a motor rotating a burr, remove heating energy, etc), or to cover the active end with a shield and sheath to prevent the active end from acting, e.g. cutting, burring, drilling, etc.

In some aspects, there is provided an apparatus for assisting tool use, the apparatus comprising:

one or more position encoders;

a wrist support;

a shaft coupled to the one or more position, wherein the shaft comprises a coupling to couple to a tool to enable a user resting a hand with the wrist on the wrist support to hold and manipulate the tool with one or more fingers of the hand; and a controller configured to:

receive encoder data from the one or more position encoders;

receiving calibration data indicative of a relationship between data from the one or more position encoders and an active end of the tool;

using the encoder and calibration data to obtain the position data indicative of a position of the active end of a tool coupled to the coupling;

receive constraint data indicative of one or more regions of space in which the active end of the tool should not be activated; and process the position and constraint data to cause generation of a control signal for the tool to deactivate the active end when a position indicated by the position data is within a region indicated by the constraint data.

It will be understood that since the encoders in these aspects can be viewed as replacing the motors, the above disclosures in the context of embodiments having one or more motors equally apply to embodiments having no motors.

In some aspects, there is provided a method to assist tool use, the method comprising:

supporting a wrist on a wrist support;

applying a force and/or torque to a tool using one or more motors disposed in a fixed relationship relative to the wrist support to constrain movement of an active end of the tool while a user resting a hand with the wrist on the wrist support holds and manipulates the tool with one or more fingers of the hand, wherein constraining the motion of the active end comprises:

receiving position data indicative of a position the active end;

receiving constraint data indicative of one or more regions of space in which the active end should not be positioned; and processing the position and constraint data to control the one or more motors to bias the active end of the tool out of the region when a position indicated by the position data is within a region indicated by the constraint data.

The method may comprise registering a coordinate system to an object to be worked on with the tool and the constraint and position data may be in a coordinate system registered to the object. The object may, for example, be part of a patient. Thus, the tool may be held and manipulated to perform surgery, for example paediatric surgery. Alternatively, the tool may be held and manipulated to perform a non-surgical task.

In some aspects, there is provided a method to assist tool use, the method comprising:

supporting a wrist of a hand on a wrist support, the hand holding and manipulating a tool having an active end;

receiving position data indicative of a position the active end from one or more position encoders fixedly disposed relative to the wrist support;

receiving constraint data indicative of one or more regions of space in which the active end should not be positioned; and processing the position and constraint data to cause generation of a control signal for the tool to deactivate the active end when a position indicated by the position data is within a region indicated by the constraint data.

In some aspects there is provided a method of performing surgery, optionally paediatric surgery, the method comprising resting a wrist of a hand on a wrist support, holding a tool with two more fingers of the hand and carrying out a surgical operation with an active end of the tool within a target region, wherein the active end of the tool is constrained to the target region by application of a restoring force and/or torque to the tool using one or more motors and the restoring force and/or torque bias the active end towards the target region when the active end is outside the target region.

In some aspects there is provided a method of making a work piece, the method comprising resting a wrist of a hand on a wrist support, holding a tool with two more fingers of the hand and carrying out a non-surgical operation with an active end of the tool within a target region of an object to make the work piece, wherein the active end of the tool is constrained to the target region by application of a restoring force and/or torque to the tool using one or more motors and the restoring force and/or torque bias the active end towards the target region when the active end is outside the target region.

In some embodiments, there is provided an apparatus for assisting tool use, the apparatus comprising: one or more motors; a wrist support; and a shaft coupled to the one or more motors. The shaft comprises a coupling to couple to a tool to enable a user resting a hand with the wrist on the wrist support to hold and manipulate the tool with one or more fingers of the hand. The apparatus further comprises a housing in which the one or more motors are disposed. The housing defines an opening and the shaft is disposed through the opening to couple to the one or more motors. The wrist support is provided on or by a top surface of the housing.

Also disclosed is the combination of this aspect with any of the above aspects and embodiments and the following embodiments are disclosed in combination with all of the above aspects and embodiments.

In some embodiments the shaft slopes away from the wrist support and in some embodiments, the opening is an elongate slot along a fore/aft direction. In some embodiments, two of the one or more motors actuate a rotational degree of freedom about a respective rotation axis each, one of the two motors actuates a linear degree of freedom along a linear axis aligned fore and aft and the rotation axes intersect in a point substantially coinciding with the linear axis. In some embodiments, the housing comprises a weighted base or clamping arrangement to maintain the housing in a substantially fixed position during operation. The one or more motors may be back driveable, thereby enabling a user to move a tool attached to the coupling without energising the one or more motors.

BRIEF DESCRIPTION OF THE FIGURES

A specific embodiment is now described by way of example to illustrate the described aspects and embodiments, with reference to the accompanying drawings, in which.

DETAILED DESCRIPTION

Figure 1:
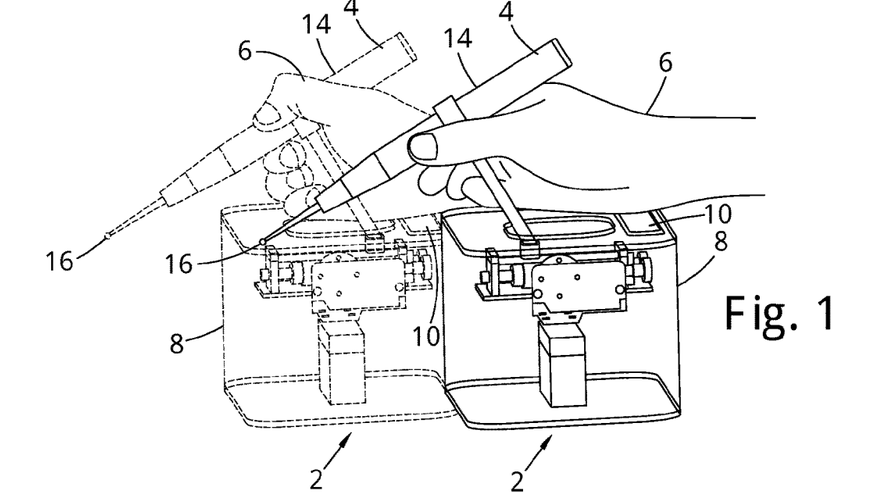
FIGS. 1 to 3 illustrate a device to assist tool use.
Figure 2:
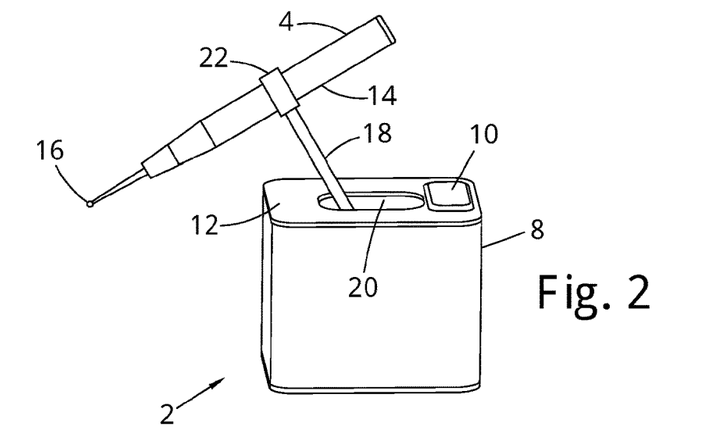
Figure 3:
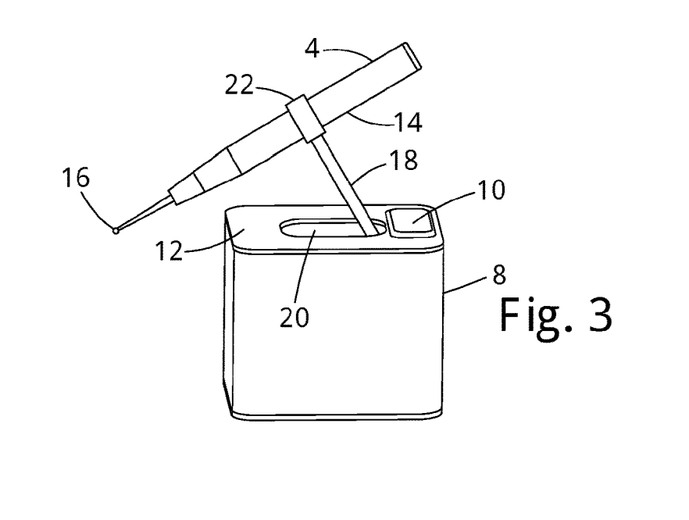

With reference to FIGS. 1 to 3, a device 2 for assisting manipulations of a tool 4 by a user using his or her hand 6 comprises a housing 8. A wrist support 10 is provided on a surface 12 of the housing 8, which, in use, is on top of the device 2. The wrist support may comprise a pad of resilient foam material, for example memory foam, to comfortably support the wrist. The tool 4 has body 14 and an active end 16, for example configured as a burr. In some embodiments, the tool is a measurement tool that can be used to gather data from a workpiece or patient, for example the size of a bone or joint. The device 2 comprises a shaft 18 extending through a slot 20 in the surface 12 of the housing 8. The shaft 18 forms a coupling 22 at one end, for engaging the body 14 of the tool 4. For example, in some embodiments the coupling 22 is configured as a ring for accepting the body 14 and comprises one or more set screws (not shown) to secure the body 14 inside the coupling 22. Of course various other embodiments of the coupling 22 to secure the body 14 will be apparent to a person skilled in the art.

The slot 20 is elongate in a direction generally along the forearm when a user rests a hand on the wrist support 10, to allow movement fore and aft of the shaft 18 by, respectively, extension and flexion of fingers of the user's hand holding the body 14 of the tool 4. The slot 20 also has extent perpendicular to the fore/aft direction to enable side to side movement of the shaft 18, as described in detail below. In some embodiments, the slot mechanically limits a range of motion of the shaft. The shaft 18 is inclined in a direction aft to fore, rising in a forwards direction away from the wrist support 10, to accommodate the slope of the user's palm when resting the wrist on the wrist support 10, in particular in an aft position when the fingers are flexed.

The housing 8 comprises a weighted base or a clamping arrangement (not shown) to dispose the housing in a substantially fixed position relative to the object to be worked on, during operation. The device 2 may also comprise a mechanically or motorised moveable positioning arrangement to aid positioning of the device 2.

Figure 4:
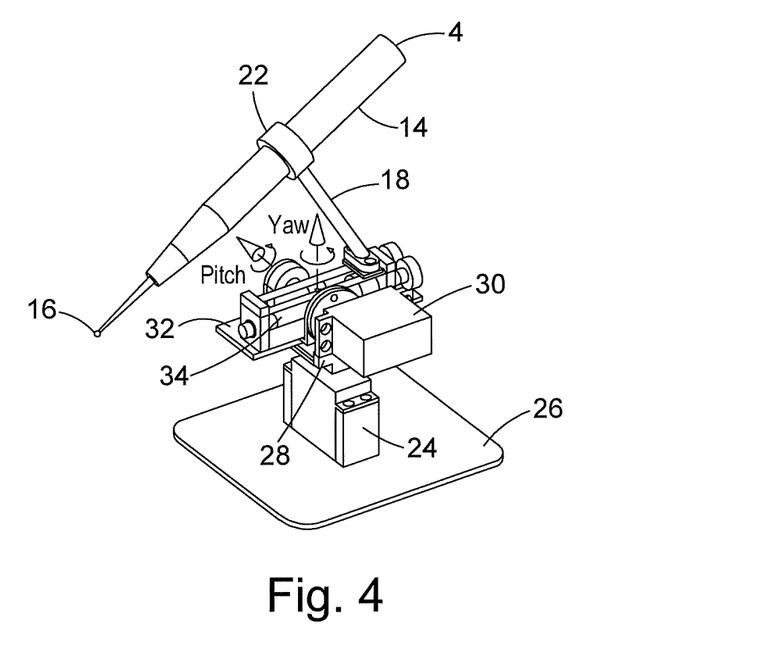
FIG. 4 illustrates a view of the device with part of its housing removed.

With reference to FIG. 4, the shaft 18 is coupled to three motors to control three corresponding degrees of freedom of the shaft 18: yaw, pitch and aft/fore movement, as illustrated in FIG. 4. A first motor arrangement 24 is secured to a base 26 of the housing 8 and controls yaw motion and torques. The output of the first motor arrangement 24 is connected to a platform 28 carrying a second motor arrangement 30, which controls pitch motion and torques. An output of the second motor arrangement 30 is secured to a platform 32 carrying a third motor arrangement 34, which controls fore and aft motion and forces. An output of the motor arrangement 34 is coupled to the shaft 18. The motor arrangements 24, 30, 34 comprise an electric motor and a low friction gearbox transmitting the torque of the electric motor to the output. In the case of the third motor arrangement 34, the gearbox comprises a worm gear or recirculating ball screw, for example, to transform the torque output to a linear motion/force output in the fore and aft direction. Of course other arrangements to generate the linear output may be used in other embodiments, including a linear motor.

The motor arrangements 24, 30, 34 are sufficiently low-friction to be back-driveable by a user exerting a force or torque on the tool 4 and hence the coupling 22, so that the user can manipulate the tool without forces or torques having to be generated by the electric motors. To this end, the force required at the coupling to overcome the back drive resistance of the motor arrangements 24, 30, 34 is less than 0.4N, preferably less than 0.3N, 0.2N, 0.1N or 0.05N. The axes of rotation of the motor arrangements 24 and 30 intersect in a point aligned (subject to tolerances) with the linear axis of translation of the motor arrangement 34, in some embodiments.

Figure 5:
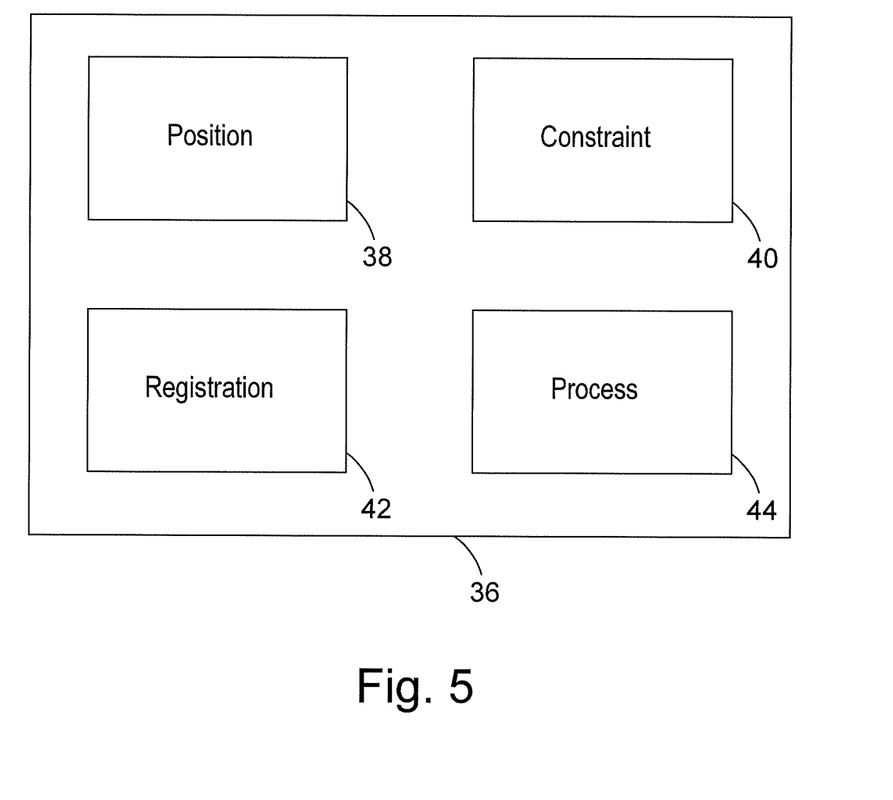
FIG. 5 illustrates a controller for the device.

With reference to FIG. 5, a controller 36 for the motor arrangements 24, 30, 34 comprises a position module 36. The position module 36 is configured to receive position data and to derive data indicative of the position of the active end 16 of the tool 4. The position data is, in some embodiments, received from encoders associated with the motor arrangements 24, 30, 34 and a position of the active end 16 is derived from this data based on knowledge of the configuration of the device 2 and tool 4, possibly after a calibration routine, if required, as is well known to a person skilled in the art. In some embodiments optical markers on the tool 4 and/or shaft 18 are detected in space using an optical detection system to measure the position and orientation of the tool 4 in place of the use of encoders.

A constraint module 40 defines one or more regions of space into which the active end 16 of the tool 4 should not enter, in some embodiments taking a model of an object to be worked on and a user input defining one or more regions as an input.

A registration module 42 contains information regarding the relative position and orientation of the device 2 and object to be worked on so that the position and constraint data can be defined in or transformed into a common coordinate system. The information may be derived using calibration during a set-up procedure, for example using a calibration tool of known configuration to acquire points on the object in device coordinates, as is well known to the person skilled in the art. For example, in case of the device being used in a surgical procedure, the points on the object may be anatomical landmarks that can be used for registration with a model of an anatomical region to be worked on with the tool 4.

A process module 44 is configured to combine information indicative of the position of the active end 16 and information indicative of the one or more regions to generate forces/torques biasing the tool 4 so that the active end 16 is moved out of the one or more regions into a region where presence of the active end 16 is undesirable, that is providing active constraints or a "virtual wall" to guide tool use. In some embodiments, the process module further or instead deactivates the active end if the active end enters one of the one or more regions. In the latter case, motors may not be required and the device may omit the motors (but retain the encoders, where applicable).

In some specific embodiments, active constraints, including the generation and definition of the one or more regions, are implemented using the techniques disclosed in any one or more of S. A. Bowyer, B. L. Davies, F. Rodriguez y Baena, IEEE Transactions on Robotics, Vol. 30, No. 1, page 138, February 2014; WO2002/060653; WO2003/043515; S. C. Ho, R. D. Hibberd and B. L. Davies, IEEE Engineering in Medicine and Biology, May/June 1995, page 292; all incorporated herein by reference. Registration techniques used in some embodiments are described in WO2003/04515 and/or WO2006/048651, both incorporated by reference herein, are used. In some embodiments, planning of the tool use using simulation as disclosed in WO2002/061688, incorporated herein by reference, is employed.

Figure 6:
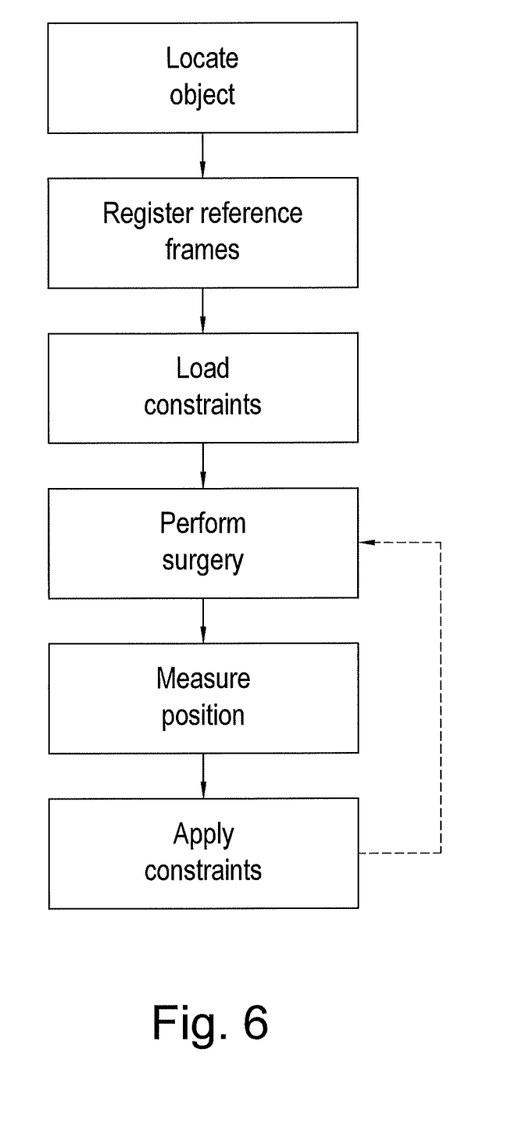
FIG. 6 illustrates a method of using the device.

With reference to FIG. 6, a method of operating the device 2 is now described in the context of surgery. However, it will be apparent that this disclosure equally applies to tool use on objects other than body parts of a patient.

At step 46, the object to be worked on, typically a body part of a patient in the case of surgery, is located relative to the device 2. The body part may be clamped in place, as is well known. The patient may be placed on a motorised bed that is moved relative to the device 2, or in some embodiments the device 2 may simply be placed next to the patient and held in place by friction or by a clamping arrangement. If not already present, a tool 4 is coupled to the device 2. These preparations may, for example, be carried out by a theatre nurse. At step 48, the frame of reference/coordinate system of the device 2 is registered with the object, as is well known and briefly described above, and constraint regions are loaded into the controller 36.

At step 50, the surgeon performs the surgery by placing a wrist on the wrist support 10 and manipulating the tool 4 with two or more fingers (or with one finger in a stall or sleeve fixed to the tool, to modify, for example cut or ablate, tissue as required by the surgery. While the surgeon performs the surgery, the position of the active end 16 of the tool is obtained, for example as described above, and the constraints are applied to urge the active end of the tool to remain in a desired region for the surgery and avoid injury to surrounding tissue. Position is obtained and constraints are applied as long as the surgeon performs the procedure with the tool 4.

The various methods executed by or in relation to the device 2 described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

A computing device implementing the disclosed methods may be integrated within the housing 8 or the disclosed apparatus may include the computing device as a separate component or separate distributed components. The computing device may operate in the capacity of a server or a client machine in a client-server network environment, or as a peer machine in a peer-to-peer (or distributed) network environment. The computing device may be a personal computer (PC), a tablet computer, a web appliance, a server, a network router, switch or bridge, or any machine capable of executing a set of instructions (sequential or otherwise) that specify actions to be taken by that machine. Further, while only a single computing device has been referenced, the term "computing device" shall also be taken to include any collection of machines (e.g., computers) that individually or jointly execute a set (or multiple sets) of instructions to perform any one or more of the methodologies discussed herein.

Unless specifically stated otherwise, as apparent from the following discussion, it is appreciated that throughout the description, discussions utilizing terms such as 'processing', 'receiving', 'deriving', 'combining' or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. Apparatus for assisting tool use, the apparatus comprising:
   one or more motors;
   a wrist support;
   a shaft coupled to the one or more motors at a first end of the shaft;
   a coupling disposed on the shaft at a second end of the shaft and configured to accept a tool to enable a user resting a hand with the wrist on the wrist support to hold and manipulate the tool with one or more fingers of the hand; and
   a controller configured to:
      receive position data indicative of a position of an active end of a tool coupled to the coupling;
      receive constraint data indicative of one or more regions of space in which the active end of the tool should not be positioned; and
      process the position and constraint data to control the one or more motors to bias the active end of the tool out of the region when a position indicated by the position data is within a region indicated by the constraint data
   wherein the one or more motors, wrist support and shaft coupling define an integrated apparatus.

2. Apparatus according to claim 1, wherein the shaft has at least one linear and at least one rotational degree of freedom.

3. Apparatus according to claim 2, wherein the at least one linear degree of freedom comprises a degree of freedom along a direction towards and away from the wrist support.

4. Apparatus according to claim 1, wherein the tool accepted by the coupling comprises a surgical tool.

5. Apparatus according to claim 1, wherein the constraint and position data are in a coordinate system registered to an object to be worked on with the tool.

6. Apparatus according to claim 1, wherein the one or more motors are back driveable, thereby enabling a user to move a tool attached to the coupling without energising the one or more motors.

7. Apparatus according to claim 1, wherein
   the one or more regions are configured to constrain a range of movement of the active end and wherein
   a largest distance between two positions of the active end within the range of movement is less than 10 cm, optionally less than 5 cm, 4 cm or 3 cm.

8. Apparatus according to claim 1, wherein
   the apparatus is configured to mechanically constrain a range of movement of the coupling and wherein
   a largest distance between two positions of the coupling within the range of movement is less than 10 cm, optionally less than 5 cm, 4 cm or 3 cm.

9. Apparatus according to claim 1, wherein the one or more motors are disposed in a housing and the wrist support is secured in relation to or is part of the housing.

10. Apparatus according to claim 1 comprising one or more position encoders, wherein each of the one or more motors is associated with a position encoder from which a configuration of the shaft along a corresponding degree of freedom can be determined and wherein receiving position data comprises:
    receiving encoder data from the one or more position encoders;
    receiving calibration data indicative of a relationship between data from the one or more position encoders and the active end of the tool; and
    using the encoder and calibration data to obtain the position data.

11. Apparatus according to claim 1, wherein the tool accepted by the coupling comprises one or more of a cutting tool, a drilling tool, a burring tool, a heating tool and a measuring tool.

12. Apparatus according to claim 5, wherein the object is part of a patient.

13. Apparatus according to claim 1, wherein the apparatus is configured as a surgical robot.

14. Apparatus according to claim 1, wherein the controller is configured to:
    process the position and constraint data to cause generation of a control signal for the tool to deactivate the active end when a position indicated by the position data is within a region indicated by the constraint data.

15. Apparatus for assisting tool use, the apparatus comprising:
    one or more motors disposed in a housing;
    a wrist support on the housing;
    a shaft extending through the housing, the shaft coupled to the one or more motors at a first end of the shaft;
    a coupling disposed on the shaft at a second end of the shaft and configured to accept a tool to enable a user resting a hand with the wrist on the wrist support to hold and manipulate the tool with one or more fingers of the hand; and
    a controller configured to:
    receive position data indicative of a position of an active end of a tool coupled to the coupling;
    receive constraint data indicative of one or more regions of space in which the active end of the tool should not be positioned; and
    process the position and constraint data to control the one or more motors to bias the active end of the tool out of the region when a position indicated by the position data is within a region indicated by the constraint data.

* * * * *